US005543303A

United States Patent [19]

Goyert

[11] Patent Number: 5,543,303
[45] Date of Patent: Aug. 6, 1996

[54] RECOMBINANT MYELOMONOCYTIC DIFFERENTIATION ANTIGEN CD14

[76] Inventor: Sanna M. Goyert, 10 Waterside Plz. #36F, New York, N.Y. 10010

[21] Appl. No.: 165,583

[22] Filed: Dec. 13, 1993

Related U.S. Application Data

[63] Continuation of Ser. No. 916,806, Jul. 22, 1992, abandoned, which is a continuation of Ser. No. 787,763, Nov. 6, 1991, abandoned, which is a continuation of Ser. No. 536,163, Jun. 8, 1990, abandoned, which is a continuation of Ser. No. 276,794, Nov. 28, 1988, abandoned.

[51] Int. Cl.$^6$ .......................... C12N 15/12; C12N 15/85; C12N 15/74; C12N 5/06
[52] U.S. Cl. .................. 435/69.1; 435/69.6; 435/240.2; 435/252.3; 435/320.1; 536/23.5; 536/24.31
[58] Field of Search .................................. 435/69.1, 69.6, 435/320.1, 252.3, 240.1, 240.2; 536/23.5, 24.31

[56] References Cited

PUBLICATIONS

Ferrero et al. (1988) Nuc. Acids Res. 16:4173.
Goyert et al. (1988) Science 239:497–500.
Goyert et al. (1987) in Leucocyte Typing III (eds. Michael et al.) Oxford U. Press. pp. 613–619.
Goyert et al (1986) J. Immunol. 137:3909–3914.
Leucocyte Typing (1984) eds. Bernard et al Spring Verlag see pp. 10, 98–100.
Dimitriu–Bona et al (1983) J. Immun R. 130:145–152.
Methods in Enzymology (1987) vol 152 Berger, et al, eds. Academic Press.
Goyert, S. et al. (1986) "Biochemistry and expression of myelomonocytic antigens" J. Immunol. 137:3909–3914.
Leucocyte Typing, ed. Bernard, A., et al. (1984) Berlin: Springer Verlag. see pp. 10, 98–100.
Dimitriu–Bona, et al. (1983) "Human Mononuclear phagocyte differentiation antigens" J. Immunol. 130 145–152.
Methods in Enzymology 152 Colowick S & Kaplan, N. (eds) Orlando. Academic Press (1987).
Ferrero, E & Goyert, S (1988) "Nucleotide sequence of the gene encoding the monocyte differentiation antigen, cd14" Nuc. Acids Res. 16:4173.
Goyert, S. et al (1988) "The CD14 monocyte differentiation antigen maps to a region encoding growth factors and receptors" Science 239:497–500.
Goyert, S & Ferrero E (1987) "Biochemical analysis of myeloid antigens and cDNA expression of GP55(cd 14)" in Leucocyte Typing III (eds) Michael, AJ., et al. Oxford University Press pp. 613–619.
Leucocyte Typing (eds. Bernard A. et al.) (1984) Berlin: Springer–Verlag see pp. 10, 98–100.
Methods in Enzymology (1987) vol. 152 Colowick S. & Kaplan N (eds) Orlando, Academic Press.
Ashmun et al (1987) Blood 69:886–892.
Haziot et al, "The Monocyte Differentiation Antigen, CD14 . . . " J. Immunol. 141(2):547–552 (Jul. 1988).
Sambrook et al, p. 16.3 in Molecular Cloning, 2nd Ed (1989).
Huyng et al, pp. 49–78 in DNA Cloning, a Practical Approach, Glover, ed., IRL Press, (1985).

Primary Examiner—Stephen G. Walsh
Attorney, Agent, or Firm—Iver P. Cooper

[57] ABSTRACT

A recombinant myelomonocytic differentiation antigen CD14 has a primary amino acid sequence substantially equivalent to that of native human CD14. A process for isolating a DNA clone pCD-CD14 encoding CD14 comprises cell surface screening of COS 7 cells transfected with expressible DNA clones by monoclonal antibodies to CD14.

12 Claims, 5 Drawing Sheets

```
CAGAATGACATCCCAGGATTACATAAACTGTCAGAGGCAGCCGAAGAGTTCACAAGCCTGAAGTGTGAAGCCTGGAAGCCGGGGTGCCGCTGTGTAGGAAAGAA
GCTAAAGCACTTCCAGAGCCTGTCCGAGCTCAGAGAGTTCGGAAGACTTATCGACCATGTGAGTGTAGGGTCTTGGGGTCGAAGCGTGCCACTCGGG

AGCCACAGGGGTTGGATGGGCCCTCCTAGACCTCTGCTCTCTCCCCAGGAGCCGCGTCCGCCTCCTGTTGCTGCTGTGCCGCTGGTGCACGTCTCT
                                                    Met GluArgAlaSerCysLeuLeuLeuLeuProLeuValHisValSer
                                                    -19                                            -10

GCGACCACGCCAGAACCTTGTGAGCTGGACGATGAAGATTTCCGCTGCGTCTGCAACTTCTCCGAACCTCAGCCCGACTGGTCCGAAGCCTTCCAGTGT
AlaThrThrProGluProCysGluLeuAspPheArgCysValCysAsnPheSerGluProGlnProAspTrpSerGluAlaPheGlnCys
-1 +1                                10                                20                            30

GTGTCTGCAGTAGAGGTGGAGATCCATGCCGGGGTCTCAACCTAGAGGCCGTTCTAAAGCCGTCGATGCGGACCCCGGACCAGTATGCTGAC
ValSerAlaValGluValGluIleHisAlaGlyValSerLeuAsnLeuGluProPheLeuLysArgValAlaAspAlaAspProArgGlnTyrAlaAsp
               40                                50                                60

ACGGTCAAGGCTCTCCGCTGCCGGCTCACAGTGGGAGCCGCACAGGTTCCTGCTCAGCTGGTAGGCGCCCTGCGTGTGCTAGGCTACTCCCGC
ThrValLysAlaLeuArgCysArgLeuThrValAlaGlyAlaGlnValProAlaGlnLeuValAlaLeuArgValAlaLeuAlaTyrSerArg
       70                                80                                90

CTCAAGGAACTGACGCTCGAGGACTTAAAGATAACCGGCACCATGCCTCCGCCTCCTGAAGCCACCAGGACTTGCACTTTCCAGCTTGCGCCTACGC
LeuLysGluLeuThrLeuGluAspLeuLysIleThrGlyThrMetProProLeuProLeuAlaThrGlyLeuAlaLeuSerLeuArgLeuArg
    100                                110                                120                           130

AACGTGTCGTGGGCGACAGGGCCGTTCTTGGCTGCCGAGCTGCCAGCAGTGGCTCAAGGCCTACTGAGACCATTGCCCAAGCACACTCCGCCT
AsnValSerTrpAlaThrGlyArgSerPheLeuAlaGluLeuLeuGlnGlnTrpLeuLysProGlyLeuLysValLeuSerIleAlaGlnAlaHisSerPro
             140                                150                                160
```

FIG. 2B

```
GCCTTTCCTGCGAACAGGTTCGCGCCTTCCCGGCCCTTACCAGCCTAGACCTGTCTGACAATCCTGGACTGGGCGAACGCGGACTGATGGCCGGCTCTC
AlaPheSerCysGluGlnValArgAlaPheProAlaLeuThrSerLeuAspLeuSerAspAsnProGlyLeuGlyLeuGluArgGlyLeuMetAlaAlaLeu
          170                        180                       190
TGTCCCCACAAGTTCCCGGCCATCCAGAATCTAGCGCTGCGCAACACAGGAATGGAGACGCCCACAGGCGTGTGCGCCACTGGCGGCGGCCAGGTGTG
CysProHisLysPheProAlaIleGlnAsnLeuAlaLeuArgAsnThrGlyMetGluThrProThrGlyValCysAlaLeuAlaAlaAlaGlyVal
          200                        210                       220                       230
CAGCCCCACAGCCTAGACCTCGCTGCGCGCCACAACTCGCTGCCCGTAAACCCTAGCGCTCCGAGATGCATGTGGTCCAGCGCCCTGAACTCCCTCAAT
GlnProHisSerLeuAspLeuSerLeuAsnSerLeuArgAlaThrValAlaProArgCysMetTrpSerSerAlaLeuAsnSerLeuAsn
          240                       250                                               260
CTGTCGTTCGCTGGGCTGGAACAGGTGCCTAAGGACTGCCAGCTGCCAAGCTCAGCTGCAACAGACTGAACAGGCGCCCAGCCT
LeuSerPheAlaGlyLeuGluGlnValProLysAspLysAspLeuSerCysAsnArgLeuAsnArgAlaProGlnPro
          270                       280                       290
GACGAGCTGCCCGAGGTGGATAACCTGACACTGGGGAATCCCCTTCCCTGGAACTGACGGGCTCAATGAACTCCGGCGTG
LeuSerPheAlaGlyLeuGluGlyLeuGluGluValLysLeuArgValLeuArgAlaProGlnProLeuAsnLeuProGlyVal
AspGluLeuProGluValAspAsnLeuThrLeuAspGlyAsnProPheLeuProGlyThrAlaLeuProHisGluGlySerMetAsnSerGlyVal
          300                       310                       320
GTCCCAGCCTGTGCACGTTCGACCCTGTCGGTGGGGTGTCGGGAACCCTGGTCGCTCCAAGGGCCCGGGGCTTTGCCTAAGATCCAAGACAGAAT
ValProAlaCysAlaArgSerThrLeuSerGlyValSerGlyValLeuLeuThrLeuValLeuLeuGlnLeuAlaArgGlyPheAla.
          330                       340                       350
AATGAATGGACTCAAACTGCCTTGGCTTCATTCATTAACAGACCTTTTCGACGACTTTCAACCCTTTGCCCACCTTTATTAAAAATC
TTAAACAACGGTTCCGTTCCTGTCGTCATTCATTAACAGACCTTAATTGCCGATATTGGATGCCGGGCACAGTACTGGATGGGAATTC
                                                                                        1570**
```

FIG. 3A

```
ACAAGTGTGAAGCCTGGAAGCCGGGGGTGCCGCTGTGTAGGAAAGAAGCTAAAGCACTTCCAGAGCCTGTCCGGAGCTCAGAGGT     86

TCGGAAGACTTATCGACCATGGAGCGCGGCTCCTGCTTGTTGTGCTGCCCGTCGTCTCTGCGGTCACGTCTCTGGCTCGTCACCGCCAGAACCT    176
                    MetGluArgAlaSerCysLeuLeuLeuLeuLeuProLeuValHisValSerAlaThrThrProGluPro
                    -19                                                     -10                -1 +1

TGTGAGCTGGACGATGAAGATTCCGCTGTCTCGAACTTCTCCGAACCTCAGCCGACTGGTCCGAAGCCTTCCAGTGTGTCTGCA     266
CysGluLeuAspAspGluAspPheArgCysValCysAsnPheSerGluProGlnProAspTrpSerGluAlaPheGlnCysValSerAla
                                    10                                  20                      30

GTAGAGGTGGAGATCCATGCCGGCGGTCTCAACCTAGAGCCCGTTTCTAAAGCCGTGGTCAAGGCCGTGGACGCCGGGCAGTATGCTGAC     356
ValGluValGluIleHisAlaGlyGlyLeuAsnLeuGluProValSerLysAlaValValLysAlaValAspAlaGlyGlnTyrAlaAsp
                40                                  50                                  60

ACGGTCAAGGCTCTCCGGTCTCGGGCTCCACAGTGGGAGCCCGACAGTTCCTGCTCAGCTACTGGTAGGCCCCTGGTGTGCTAGCG     446
ThrValLysAlaLeuArgValArgArgLeuThrValGlyAlaAlaGlnLeuLeuLeuValGlyAlaLeuArgValAlaLeuAla
                70                                  80                                  90

TACTCCCGCCTCAAGGAACTGACGCTGGAGGACCTAAAGATAACCGGACTGTACGGGACCATGCCTCCGGAAGCCACAGGACTTGCACTT     536
TyrSerArgLeuLysGluLeuThrLeuGluAspLeuLysIleThrGlyLeuTyrGlyThrMetProProLeuGluAlaThrGlyLeuAlaLeu
                100                                 110                                 120

TCCAGCTTGCGGCGCCAACGTGTCTGGGCGACAGGCGTTCTTGGCTGCCGAGCTGGCTCAAGCCAGCCTCAAGCCTGGCTTGAAGGTA     626
SerSerLeuArgArgAsnValSerArgAlaThrGlyArgSerTrpAlaThrGlyValLeuLeuGlnTrpLeuLeuLysProGlyLeuLysVal
                130                                 140                                 150

CTGAGCATTGCCCAAGCACACTGCCTTTCCTGGAACAGGTTCGGCCCTTCCCGGGCCCTTACCAGCCTAGACCTGTCTGACAAT     716
LeuSerIleAlaGlnAlaHisSerProAlaPheSerCysGluGlnValArgAlaPheProAlaLeuThrSerLeuAspLeuSerAspAsn
                160                                 170                                 180
```

FIG. 3B

```
CCTGGACTGGGCGAACGCGGACTGATGGCGGCTCTCTGTCCCCACAAGTTCCCGGCCATCCAGAATCTAGGCGCTGGCGCAACACAGGAATG  806
ProGlyLeuGluGlyArgGlyLeuMetAlaAlaLeuAlaLeuCysProHisLysPheProAlaIleGlnAsnLeuAlaLeuArgAsnThrGlyMet
                   190                               200                               210

GAGACGCCCACAGGCGTGTCGCCCCACTGGCGGGCCAGTGTGCAGCCCCACAGCCCCAGACCTAGACCTAGACCCCACAGCCTCGCGGCCACC  896
GluThrProThrGlyValCysAlaAlaLeuAlaLeuAlaAlaGlyValGlnProHisSerLeuAspLeuSerHisAsnSerLeuArgAlaThr
                   220                               230                               240

GTAAACCCTAGCCGCTCCGAGATGCATGTGGTCCAGCGCCCTGAACTCCCTCAATCTGTCGTTCCGCTGGGCTGGAACAGGTGCCTAAAGGA  986
ValAsnProSerGlyMetTrpSerSerAlaLeuAsnSerLeuAsnSerPheAlaGlyLeuGluGlnValProLysGly
                   250                               260                               270

CTGCCAGCCAAGCTCAGAGTCGATCTCAGCTGCAACAGACTGAACAGGGCGCCCCAGCCTGACGAGCTGCCCGAGGTGGATAACCTG  1076
LeuProAlaLysLeuArgValLeuAspLeuSerCysAsnArgLeuAsnArgAlaProGlnProAspGluLeuProGluValAspAsnLeu
                   280                               290                               300

ACACTGGACGGGAATCCCTTCCTGGTCCCCTCCCCCACCGAGGGCTCAATGAACTCCGGCGTGGTCCCAGCCTGTGCACGT  1166
ThrLeuAspGlyAsnProPheLeuValProProHisGluGlySerMetAsnSerGlyValValProAlaCysAlaArg
                   310                               320                               330

TCGACCCTGTCGGTGGGGTGTCGGGAACCCTGGTGCTGCTCCAAGGGCCCGGGCCTTTGCCTAAGATCCAAGACAGAATAATGAATGG  1256
SerThrLeuSerValGlyValSerGlyThrLeuValLeuLeuLeuGlnGlyAlaArgGlyPheAla
                   340                               350                   End

ACTCAAACTGCCTTGGCTTCAGGGAGTCCCGTCAGGACGTTGAGGACTTTCGACCAATTCAACCCTTTGCCCCACCTTTATTAAAATC  1346
TTAAACAACAAAAAAAAAAAA
```

RECOMBINANT MYELOMONOCYTIC DIFFERENTIATION ANTIGEN CD14

The U.S. Government has a paid-up license in this invention and the right in limited circumstances to require the patent owner to license others on reasonable terms as provided for by the terms of Grant AI 23859, awarded by the National Institutes of Health.

This application is a continuation of application Ser. No. 07/916,806, filed Jul. 22, 1992, now abandoned, which is a continuation of application Ser. No. 07/787,763, filed Nov. 6, 1991, now abandoned, which is a continuation of 07/536,163 filed Jun. 8, 1990, now abandoned, which is a continuation of 07/276,794, filed Nov. 28, 1988, now abandoned, all incorporated by reference herein.

BACKGROUND OF THE INVENTION

The present invention relates to a myelomonocytic differentiation antigen and, more particularly to CD14.

Differentiation of myelomonocytic cells from pluripotent stem cells to mature, functioning monocytes/macrophages and granulocytes is accompanied by a variety of changes including the expression of new cell surface antigens. [K. A. Foon and R. F. Todd III, Blood 68, 1 (1986).] One such antigen, CD14, recognized by a number of monoclonal antibodies (mAbs) including MO2, MY4, and LeuM3 [S. M. Goyert et al., *J. Immunol.* 137, 3909 (1986); S. M. Goyert and E. Ferrero, in *Leukocyte Typing III*, A. McMichael et al., Eds. (Oxford Univ. Press, Oxford, 1987), pp. 613–619], is a 53-kDa glycoprotein expressed by monocytes, macrophages [R. F. Todd III et al., in *Leukocyte Typing*, A. Bernard, L. Boumsell, J. Dausset, C. Milstein, S. F. Schlossman, Eds. (Springer-Verlag, New York, 1984), pp. 424–433; J. D. Griffin and S. F. Schlossman, ibid., pp. 404–410; N. Hogg and M. A. Horton, in *Leukocyte Typing III*, A. McMichael et al., Eds. (Oxford Univ. Press, Oxford, 1987), pp. 576–602], and activated granulocytes [N. Hogg and M. A. Horton, in *Leukocyte Typing III*, A. McMichael et al., Eds. (Oxford Univ. Press, Oxford, 1987), pp. 576–602; C. Buckle and N. Hogg, personal communication].

The restricted expression of this molecule on mature cells suggests an important effector function.

The CD14 gene is located in a region of chromosome 5 containing a cluster of genes that encode several myeloid-specific growth factors [interleukin-3, granulocyte-macrophage colony-stimulating factor, and macrophage colony-stimulating factor (CSF-1) or growth factor receptors (FMS, receptor for CSF-1) [M. M. LeBeau et al., ibid. 231, 984 (1986); M. M. LeBeau et al., *Proc. Natl. Acad. Sci. U.S.A.* 84,5913 (1987); M. J. Pettenati et al., ibid., p. 2970], as well as other growth factor and receptor genes [platelet-derived growth factor receptor, B2-adrenergic receptor, and endothelial cell growth factor [HGM9: Ninth International Workshop on Human Gene Mapping (1987), *Cytogenet. Cell Genet.*, in press]. The mapping of the CD14 gene to this region of chromosome 5, its expression preferentially by mature myeloid cells, and its deletion in the malignant cells of patients having myeloid leukemias and a del(5q) suggest that the CD14 antigen may also serve as some type of receptor or factor and that a role for this gene in the pathogenesis of myeloid disorders should be considered. The CD14 antigen is thus useful in the diagnosis of mature myeloid leukemia.

The potential uses of CD14 in the medical and scientific fields are, of course, limited by its natural availability.

Accordingly, it is an object of the present invention to provide recombinant myelomonocytic differentiation antigen CD14.

Another object is to provide such protein which has a primary amino acid sequence substantially equivalent to that of native human CD14.

A further object is to provide a recombinant DNA sequence which comprises the coding sequence for CD14.

Still another object is to provide a replicative cloning vector which comprises the sequence encoding CD14 or a portion thereof and a replicon operative in prokaryotic or eukaryotic cells.

It is also an object to provide an expression system which comprises a DNA sequence encoding CD14 operably linked to suitable control sequences.

It is another object to provide recombinant host cells transformed with such an expression system.

It is a further object to provide a method of producing recombinant CD14.

Another object is to provide a clone of CD14.

A still further object is to provide a process for isolating a DNA clone encoding CD14.

SUMMARY OF THE DISCLOSURE

Figure 3A:
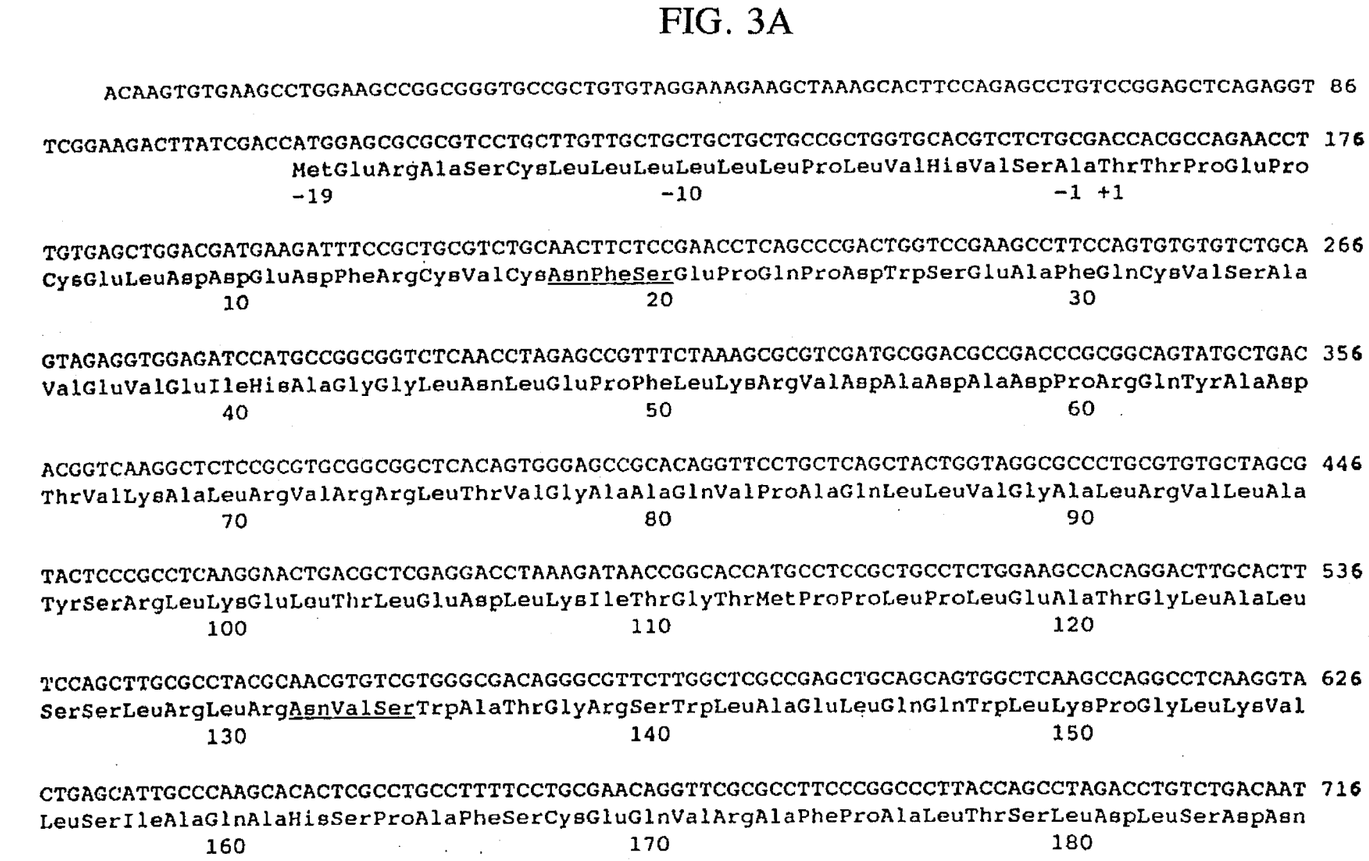
FIG. 3 is a chart of the nucleotide sequence of the cDNA encoding CD14 and its deduced amino acid sequence.
Figure 3B:
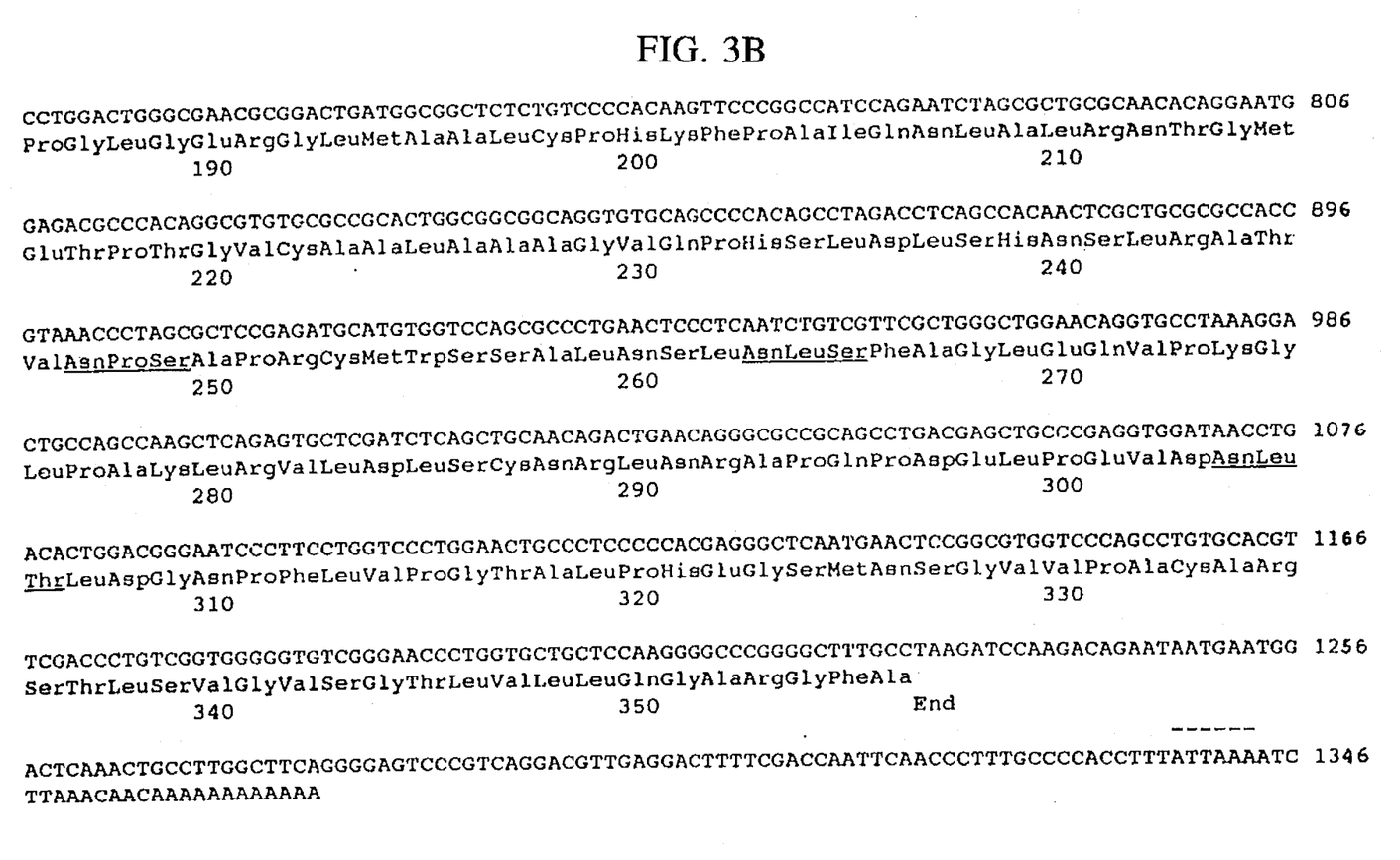

It has now been found that the above and related objects of the present invention are obtained in recombinant or eukaryotic myelomonocytic differentiation antigen CD14. In a preferred embodiment, the protein has a primary amino acid sequence substantially equivalent to that of native human CD14. The recombinant protein has the N-terminal amino acid sequence and an internal amino acid sequence as shown in FIG. 3. The recombinant protein is substantially free of glycosylation in prokaryotic cells and glycosylated in eukaryotic cells.

Another aspect of the present invention is a recombinant DNA sequence which comprises the coding sequence for CD14. In a preferred embodiment, the recombinant sequence encodes human CD14, especially human CD14 having a primary amino acid sequence substantially equivalent to that of native human CD14. The recombinant sequence has the genomic structure shown in FIG. 2 and a cDNA structure shown in FIG. 3.

A further aspect of the present invention is a replicative cloning vector which comprises the sequence encoding CD14 or a portion thereof encoding the sequential amino acids which define the functioning sites, and a replicon operative in eukaryotic or prokaryotic cells. Preferably the sequence encoding CD14 encodes a protein which has a primary amino acid sequence substantially equivalent to that of a native human CD14, optimally a protein of substantially equivalent amino acid sequence as that encoded in CD14.

Still another aspect of the present invention is an expression system which comprises a DNA sequence encoding CD14 operably linked to suitable control sequences.

In a preferred embodiment, the sequence encoding CD14 encodes a protein which has a primary amino acid sequence substantially equivalent to that of native human CD14, optimally a protein of Substantially equivalent amino acid sequence as that encoded in pCD-CD14. The expression system is disposed in a vector capable of replication in suitable host cells. The present invention also encompasses recombinant host cells transformed with such an expression system, and a method of producing recombinant CD14 which comprises culturing the recombinant host cells.

The present invention is also directed to the clone pCD-CD14 and to a process of isolating a DNA clone encoding CD14 which comprises cell surface screening of COS 7 cells transfected with expressible DNA clones with monoclonal antibodies to CD14. Preferably the CD14 is mammalian CD14 and the antibodies are produced by a mammal immunized against mammalian CD14, e.g., mice immunized with human CD14. The present invention also encompasses recombinant CD14 produced by the clone isolated by the process.

Figure 2B:
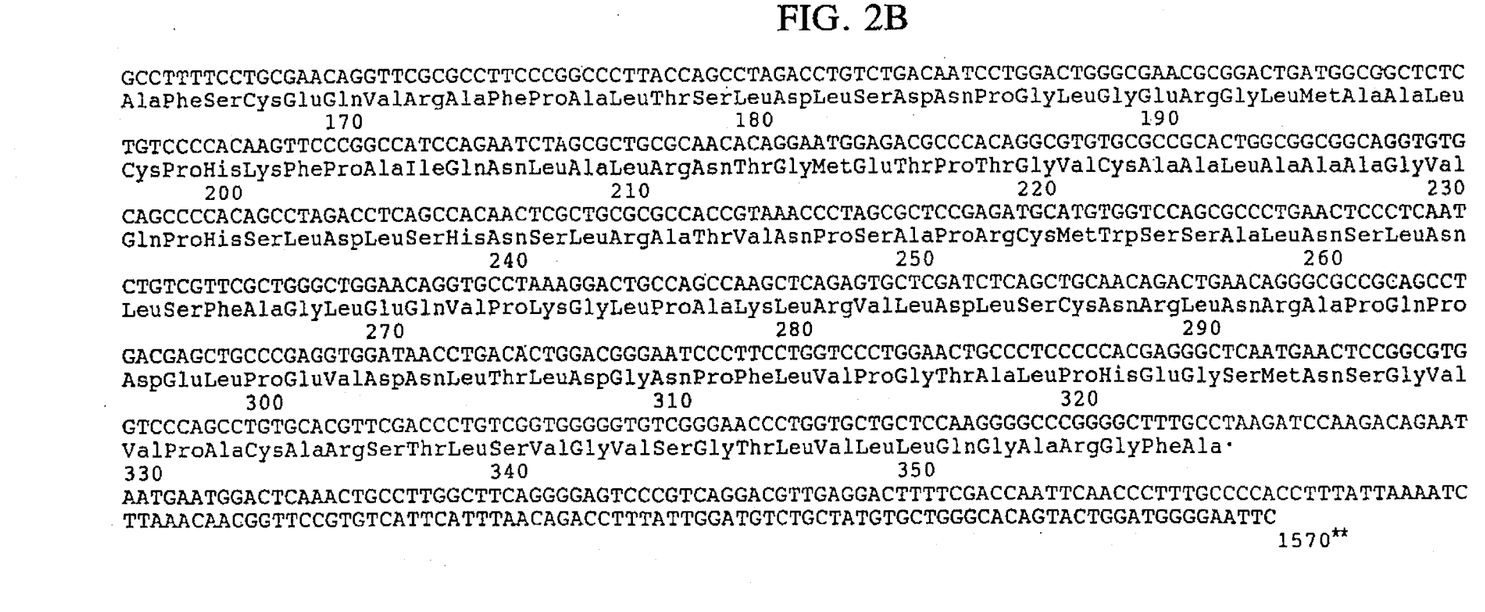
FIG. 2 is a chart of the nucleotide sequence of the gene encoding CD14 and the amino acid sequence of CD14 deduced from the cDNA sequence.

The present invention is further directed to a DNA fragment comprising the sequence selected from the group consisting of the DNA sequences set forth in FIG. 2.

BRIEF DESCRIPTION OF THE DRAWING

The above brief description, as well as further objects and features of the present invention, will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

A complementary DNA (cDNA) clone encoding CD14 was isolated by means of a novel method that includes cell surface screening with monoclonal antibodies of COS 7 cells transfected with expressible cDNA clones. In addition, the CD14 gene was isolated, characterized, and found to be located on chromosome 5 in a region containing a number of growth factor and receptor genes.

The recombinant CD14 protein will be substantially free of glycosylation if produced in prokaryotic cells. However, if produced in eukaryotic cells, it will be glycosylated. The native protein is glycosylated.

THE CD14 CLONE

A cDNA library was constructed in the Okayama/Berg eukaryotic expression vector, pCD [H. Okayama and P. Berg, Mol. Cell. Biol. 3, 280 (1983)], with messenger RNA (mRNA) isolated from M4-AML (myelomonocytic) cells, which express high levels of CD14 [S. M. Goyert et al., Science 239,497 (1988)]. A cDNA clone encoding CD14 was isolated by immunofluorescent analysis of transfected COS 7 cells, with a mAb to CD14.

Since removal of N-linked carbohydrate from CD14 reduces its molecular weight from 53 kDa to approximately 45 kDa [S. M. Goyert et al., J. Immunol. 137, 3909 (1986)], a cDNA of at least 1.3 kb would be necessary to encode the protein moiety. Therefore, the cloned cDNA was size-selected on low-melting agarose gels to contain inserts of 1.0 to 2.65 kb [T. Yokota et al., Proc. Natl. Acad. Sci. U.S.A. 81, 1070 (1984); S. M. Goyert et al., Science 239, 497 (1988)]. Escherichia coli (RR1) were then transformed with a portion of the DNA and plated on agar. A total of 1056 colonies were randomly selected, transferred individually to small liquid cultures, and grown overnight at 37° C. Pools of 24 plasmids each were prepared, giving a total of 44 pools. Each pool was grown in 500 ml of Luria broth containing 100 ug of ampicillin per milliliter, and the plasmid DNA was isolated and used to transfect COS 7 cells [S. M. Goyert et al., Science 239, 497 (1988)]. Expression of cell surface CD14 molecules was determined by indirect immunofluorescence [Ibid.] with the monoclonal antibody to CD14, MOS39 [A. Dimitriu-Bona, G. R. Burmester, S. J. Waters, R. J. Winchester, J. Immunol. 130, 145 (1983)], and fluoresceinated sheep antibody to mouse immunoglobulin. Each of the 44 plasmid pools was analyzed for cell surface expression and 5 were found that produced CD14 expression. Each of the 24 plasmids from one of the positive pools was isolated on a cesium chloride gradient, transfected individually into COS 7 cells, and assayed as described above. One cDNA clone, pCD-CD14, was found to express CD14.

pCD-CD14 was inserted into the lambda NMT vector and used to stably transfect U251-Mg cells. Analysis of the recombinant CD14 protein expressed by these cells (as well as normal monocytes) indicates that it is anchored to the membrane by a glycosyl phosphatidylinositol (GPI) linkage. Three forms of the CD14 protein can be isolated from these transfected cells (U251-CD14) including form I, the cell surface form, form II, the form released by an enzyme which cleaves GPI-anchored proteins (the enzyme is called phosphatidylinositol-phospholipase C [PI-PLC]], and form III, a form which is smaller in molecular weight (48 Kda) than forms I (53 KDa) and II (53 KDa) and which is spontaneously released into U251-CD14 culture supernatants [Haziot, A. et al., J. Immunnol., 141, 547–552 (1988)].

CONFIRMATION OF CD14 CLONE

To confirm that this clone, pCD-CD14, encodes authentic CD14 molecules, CD14 immunoprecipitates prepared from pCD-CD14-transfected COS 7 cells and from M4-AML cells expressing endogenous CD14 were compared by SDS-polyacrylamide gel electrophoresis (PAGE). The molecules precipitated from both sources were nearly identical in size [S. M. Goyert et al., J. Immunol. 137, 3909 (1986)].

Northern blot analysis was used to determine whether the clone pCD-CD14 hybridized with mRNA expressed at the appropriate stages of differentiation. RNA isolated from cells representing different stages of myeloid differentiation as well as different cell lineages was analyzed for its ability to bind the pCD-CD14 probe. The probe was found to hybridize to a single mRNA species that showed an expression profile identical to CD14; it was present in monocytes, granulocytes and M4-AML cells, but not in less mature myeloid cells represented by the leukemic cell lines K562 (undifferentiated), U937 (monoblast-like), HL60 (promyelocyte-like), or M2-AML (myeloblastic with maturation) cells or lymphocytes [S. M. Goyert et al., Science 239,497 (1988)].

Figure 1:
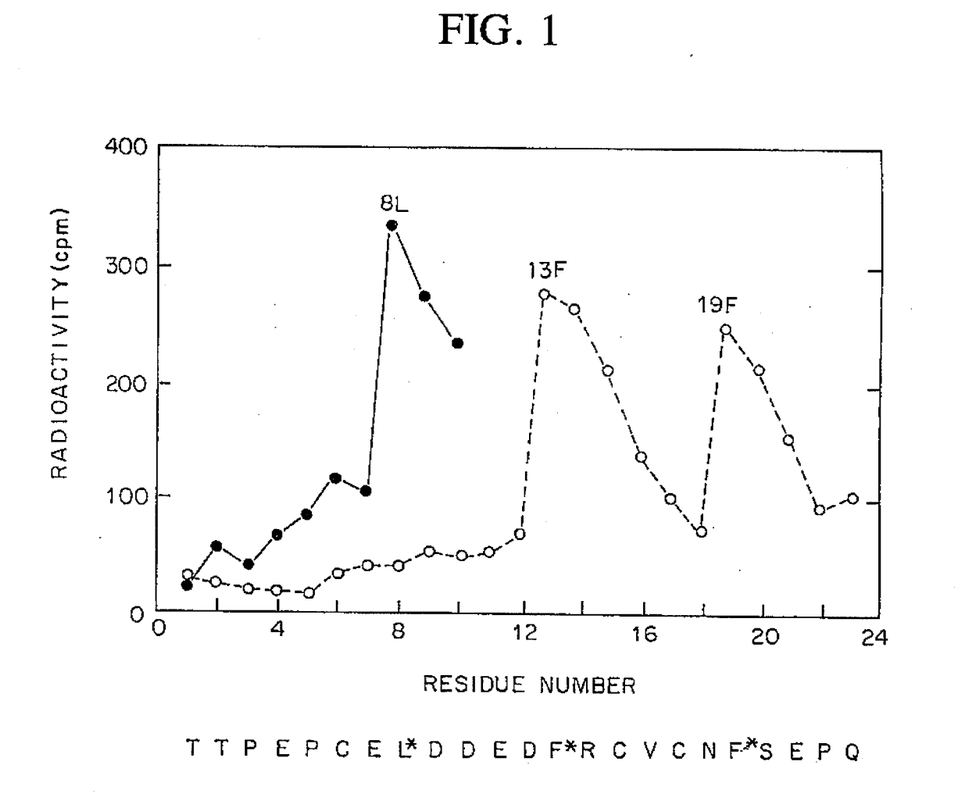
FIG. 1 is a graph of the partial $NH_2$-terminal sequence of the CD14 cell surface protein and a comparison thereof to the amino acid sequence deduced from cDNA.

Finally, the predicted protein sequence of the pCD-CD14 clone corresponded to the partial protein sequence of CD14 determined by microsequence analysis. The partial $NH_2$-terminal sequence of the CD14 cell surface protein was compared to the amino acid sequence deduced from cDNA. The partial $NH_2$-terminal amino acid sequence of CD14 molecules purified from M4-AML cells by immunoprecipitation and SDS-PAGE was determined by radioactive sequence analysis of [$^3$H]leucine- and [$^3$H]phenylalanine-labeled proteins. More particularly, M4-AML cells ($2\times10^8$) were labeled in culture with either ($^3$H) leucine (L. New England Nuclear) or [³H]phenylalanine (F), and CD14 molecules were isolated with mAb MOS39 by affinity chromatography and SDS-PAGE as previously described [S.M. Goyert et al., Science 239, 497 (1988); S.M. Goyert, J. E. Shivley, J. Silver, J. Exp. Med. 156, 550 (1982)]. After elution from 10% polyacrylamide gels, samples were dialyzed extensively against 0.01% SDS, lyophilized, redissolved in water, and applied to an Applied Biosystems gasphase amino acid sequencer. The sequentially released residues were analyzed for the presence of $^3$H in a scintillation counter. Counts above background were plotted on a linear graph, as illustrated in FIG. 1. The [$^3$H] leucine sample was sequenced for 10 cycles and the [$^3$H]phenylalanine sample was sequenced for 23 cycles. A leucine residue (solid line) was detected at amino acid position 8 and phenylalanine residues (broken line) were detected at positions 13 and 19. The protein sequence (as indicated by the one-letter amino acid code) of CD14 deduced from the cDNA clone is shown under the graph. Abbreviations for the amino acid residues are: C, Cys; D, Asp; E, Glu; F, Phe; L, Leu; N, Asn; P, Pro; Q, Gln; R, Arg; S, Ser; T, Thrl and V, Val. As can be seen, leucine and phenylalanine residues (*) are found at identically spaced positions near the NH$_2$-terminus of the pCD-CD14-predicted protein sequence. These results establish the NH$_2$-terminal amino acid of the maitre protein as threonine and indicate that the mature cell surface protein is composed of 356 amino acids.

THE CD14 GENE

The CD14 gene was isolated from a size-selected (6-kb average) Eco RI genomic library constructed in the lambda vector gtWes. DNA sequence analysis indicates, as shown by the nucleotide sequence of the gene illustrated in FIG. 2, that it contains a single intron of 88 base pairs immediately after the ATG translational start site. The initiation codon is flanked by a sequence which shows homology to the consensus sequence $C(C)_G{}^A CCATGG$ for a translation initiation site defined by Kozak [Kozak, M., Nucl. Acids Res. 15, 8125–8148 (1987)] and is separated from the rest of the coding region by the 88 bp intron. The cDNA polyadenylation signal (ATTAAA) is overlined.

As illustrated in FIG. 3, the pCD-CD14 cDNA clone was found to consist of 1367 nucleotides with a polyadenylate tail at the 3' end. An initiation codon was identified at position 105, followed by an open reading frame (coding region) consisting of 1125 nucleotides (+108 to +1233) and flanked by 104 nucleotides of 5' untranslated sequence and 126 nucleotides of 3' untranslated sequence. Comparison with the partial protein sequence determined by microsequence analysis confirms the identity of this clone as encoding CD14 (see FIG. 1) and indicates the presence of a signal peptide of 19 amino acids (−19 to −1 ).

The CD14 protein sequence contains several features characteristic of cell surface glycoproteins. These include a stretch of 17 hydrophobic and neutral amino acids at the COOH-terminus, which could serve as a membrane anchor, and five potential sites for N-linked glycosylation (underlined in FIG. 3). Comparison of the CD14 nucleotide and predicted protein sequences to all sequences in the Bionet data bank shows no significant homologies.

Southern blot analysis of DNA digested with several different restriction enzymes and probed with CD14 cDNA gave single bands, suggesting that CD14 is encoded by a single gene.

An expression system for CD14 comprises a DNA sequence encoding CD14 operably linked to suitable control sequences. The control sequences may be either from the CD14 gene itself or from other genes and/or vectors including pCD (SV40 promoter) or other available heterologous promoters.

CD14 GENE LOCATION

The chromosomal location of the human CD14 gene (CD14) was determined by analysis of DNA from mouse-human somatic cell hybrids [S. M. Goyert et al., Science 239, 497 (1988)]. Southern blot analysis was used on Eco RI digests of DNA isolated from human, mouse, and selected human×mouse hybrids. Restriction endonuclease-digested genomic DNA was separated on 0.7% agarose gels, transferred to nitrocellulose, and hybridized with $^{32}$P-labeled nick-translated CD14 cDNA [J. M. Chirgwin, A. E. Przybyla, R. J. MacDonald, W. J. Rutter, Biochemistry 18, 5294 (1979)]. Filters were washed in 0.3×standard saline citrate with 0.1% SDS at 65° C. Of 21 hybrid clones, 6 were positive for the 5.5-kb Eco RI gene fragment. These six hybrids were found by karyotype analysis and testing for human isoenzymes, cell surface antigens, and DNA markers [W. J. Rettig et al., Proc. Natl. Acad. Sci. U.S.A. 81, 6437 (1984); W. J. Rettig et al., J. Exp. Med. 162, 1603 (1985); N. C. Dracopoli et al., Proc. Natl. Acad. Sci. U.S.A. 83, 1822 (1986)] to contain human chromosome 5, but to have no other human chromosome in common. Furthermore, none of the 15 hybrids that were negative for human CD14 contained a complete copy of human chromosome 5.

The results of a discordancy analysis for the chromosomal assignment of human CD14 are listed in Table 1. Presence or absence of human CD14 was determined by Southern blot analysis of Eco RI-digested hybrid cell DNA with a $^{32}$P-labeled nick-translated CD14 cDNA probe. Numbers listed refer to hybrids showing discordance for the presence of specific human chromosomes and human CD14; deleted or rearranged copies of human chromosomes were not evaluated.

In situ chromosomal hybridization [M. M. LeBeau, C. A. Westbrook, M. O. Diaz, J. D. Rowley, Nature (London) 312, 70 (1984)] of the $^3$H-labeled pCD-CD14 probe to normal human metaphase cells resulted in specific labeling only of chromosome 5 [S. M. Goyert et al., Science 239, 497 (1988)]. The labeled sites were clustered at 5q22-q32; the largest cluster of grains was located at 5q23-q31. To determine the distribution of labeled sites on chromosome 5 in normal human metaphase cells that were hybridized with the CD14 probe, 100 metaphase cells were examined. 36 (36%) were labeled on region q2 or q3 of one or both chromosome 5 homologs. Of 182 labeled sites observed, 50 (27.5%) were located on this chromosome. These sites were clustered at bands q22 to q32, and this cluster represented 22.5% (41/182) of all labeled sites (cumulative probability for the Poisson distribution is less than 0.0005). The largest number of grains was located at 5q23 to q31. All hybridizations were repeated three times and gave similar results in each experiment. Human metaphase cells were prepared from phytohemagglutinin-stimulated peripheral blood lymphocytes. Radiolabeled CD14 probes were prepared by nick translation of the entire plasmid with all four $^3$H-labeled deoxynucleoside triphosphates to a specific activity of 1.0×10$^8$ dpm/ug. In situ hybridization was performed as previously described [M. M. LeBeau, C. A. Westbrook, M. O. Diaz, J. D. Rowley, Nature (London) 312, 70 (1984)]. Metaphase cells were hybridized at 4.0 and 8.0 ng of probe per milliliter of hybridization mixture. Autoradiographs were exposed for 11 days.

The localization of the gene encoding CD14 (a differentiation antigen specifically expressed by myeloid cells) to 5q23-q31 is particularly interesting in light of the nonrandom chromosomal deletions in human myeloid disorders that involve this chromosome region. Loss of a whole chromosome 5 or loss of a part (deletion) of the long arm of this chromosome [del(5q)] is frequently observed in the malignant cells of patients with a myelodysplastic syndrome [(MDS) 5 to 10%], therapy-related acute nonlymphocytic leukemia [(t-ANLL) 50%], or acute nonlymphocytic leukemia de nova [(ANLL) 10%][M. LeBeau et al., *J. Clin. Oncol.* 4, 325 (1986); H. Van den Berghe, K. Vermaelen, C. Mecucci, P. Barbieri, G. Tricot, *Cancer Genet. Cytogenet.* 17, 189 (1985); G. W. Dewald, M. P. Davis, R. V. Pierre, J. R. O'Fallon, H. C. Hoagland, *Blood* 66, 189 (1985)]. Although there is variability in the breakpoints of these interstitial deletions, cytogenetic analysis has revealed that one segment of chromosome 5 is deleted in all patients who have this cytogenetic abnormality [M. M. LeBeau et al., *J. Clin. Oncol.* 4, 325 (1986)]; this segment, called the critical region, consist of bands 5q23-q31. The identification of such a region suggests that loss of a critical DNA sequence leading to hemizygosity (or homozygosity) of a recessive allele may play an important role in the pathogenesis of these disorders. Such a mechanism has been substantiated recently for retinoblastoma [W. H. Lee et al., *Science* 235, 1394 (1987). To determine the relation of the CD14 gene to the critical region of chromosome 5, the pCD-CD14 probe was hybridized to metaphase cells obtained from bone marrow aspirates of five patients who had an MDS (5q-syndrome), ANLL de novo, or t-ANLL characterized by a del(5q). This resulted in specific labeling of the normal chromosome 5 homologs, but not of the rearranged homologs, indicating that the CD14 locus was deleted as a result of an interstitial deletion of 5q.

The CD14 gene is located in a region of chromosome 5 containing a cluster of genes that encode several myeloid-specific growth factors or growth factor receptors, as well as other growth factor and receptor genes. The mapping of the CD14 gene to this region of chromosome 5, its expression preferentially by mature myeloid cells in cell surface and soluble forms, and its deletion in the malignant cells of patients having myeloid leukemias and a del(5q) suggest that the CD14 antigen may also serve as some type of receptor or factor and that a role for this gene in the pathogenesis of myeloid disorders should be considered.

To summarize, the present invention provides recombinant myelomonocytic differentiation antigen CD14, a protein having a primary amino acid sequence substantially equivalent to that of native human CD14. The present invention further provides a recombinant DNA sequence which comprises the coding sequence for CD14, a replicative cloning vector which comprises the sequence encoding CD14 (or a portion thereof) and a replicon operative in prokaryotic or eukaryotic cells, an expression system which comprises a DNA sequence encoding CD14 operably linked to suitable control sequences, recombinant host cells transformed with such an expression system, and a method of producing recombinant CD14. The present invention also provides a clone of CD14 and a process for isolating a DNA clone encoding CD14. In brief, the present invention provides means for obtaining CD14 or a clone thereof in the relative abundance required for both scientific and medical uses.

Now that the preferred embodiments of the present invention have been shown and described in detail, various modifications and improvements thereon will become readily apparent to those skilled in the art. Accordingly, the appended claims are to be construed broadly and in a manner consistent with the spirit and scope of the present invention herein.

I claim:

1. A non-naturally occurring recombinant DNA molecule comprising a first DNA sequence selected from the group consisting of
   (a) a cDNA sequence encoding mature human CD14, as set forth in FIG. 3, or the genomic DNA sequence encoding mature human CD14, as set forth in FIG. 2;
   (b) a DNA sequence which specifically hybridizes to the noncoding strand of (a) above and which codes on expression for a polypeptide specifically recognized by an antibody which also specifically recognizes human CD14; and
   (c) a DNA sequence which encodes the same polypeptide as is encoded by a DNA sequence of (a) or (b) above;
   said molecule further comprising one or more vector DNA sequences rendering the molecule capable of replication in a host cell, said molecule further comprising one or more control sequences operably linked to said first DNA sequence, whereby said first DNA sequence can be expressed in a host cell in which said control sequences are functional and at least one of said control sequences is one which, in nature, is not operably linked to said first DNA sequence.

2. The recombinant DNA molecule of claim 1 in which the molecule is a plasmid.

3. A cell transformed with the recombinant DNA molecule of claim 1, said molecule replicating in said cell, and said control sequences being functional in said cell.

4. The cell of claim 3, where the cell is not a mouse cell.

5. A method of producing a peptide or protein which comprises cultivating the cell of claim 3 under conditions conducive to expression of the first DNA sequence and recovering its mature expression product.

6. The method of claim 5 in which the cell is a mammalian cell.

7. The method of claim 6 in which the mature expression product is glycosylated.

8. The method of claim 5 in which the cell is a bacterial cell and the mature expression product is not glycosylated.

9. A non-naturally occurring recombinant DNA molecule comprising a first DNA sequence selected from the group consisting of
   (a) a cDNA sequence encoding mature human CD14, as set forth in FIG. 3, or the genomic DNA sequence encoding mature human CD14, as set forth in FIG. 2;
   (b) a DNA sequence which specifically hybridizes to the noncoding strand of (a) above and which codes on expression for a polypeptide specifically recognized by an antibody which also specifically recognizes human CD14; and
   (c) a DNA sequence which encodes the same polypeptide as is encoded by a DNA sequence of (a) or (b) above;
   where said recombinant DNA molecule does not comprise any DNA sequence, other than the native sequence of the human CD14 gene, which is specific to another human gene carried by the human chromosome which bears the CD14 gene.

10. A non-naturally occurring recombinant DNA molecule comprising a first DNA sequence selected from the group consisting of
    (a) a cDNA sequence encoding mature human CD14, as set forth in FIG. 3, or the genomic DNA sequence encoding mature human CD14, as set forth in FIG. 2;

(b) a DNA sequence which specifically hybridizes to the noncoding strand of (a) above and which codes on expression for a polypeptide specifically recognized by an antibody which also specifically recognizes human CD14; and (c) a DNA sequence which encodes the same polypeptide as is encoded by a DNA sequence of (a) or (b) above;

where said first DNA sequence is flanked by predetermined restriction sites whereby it may be excised, using a restriction enzyme, from said recombinant DNA molecule.

11. A purified DNA molecule consisting essentially only of at least one strand of a first DNA sequence selected from the group consisting of:

(a) a cDNA sequence encoding mature human CD14, as set forth in FIG. 3, or the genomic DNA sequence encoding mature human CD14, as set forth in FIG. 2;

(b) a DNA sequence which specifically hybridizes to the noncoding strand of (a) above and which codes on expression for a polypeptide specifically recognized by an antibody which also specifically recognizes human CD14; and (c) a DNA sequence which encodes the same polypeptide as is encoded by a DNA sequence of (a) or (b) above;

optionally including the control sequences native to the human CD14 gene.

12. The DNA molecule of claim 11, in labeled form.

* * * * *